United States Patent
Gorrie

[11] 3,934,582
[45] Jan. 27, 1976

[54] SURGICAL WRAP
[75] Inventor: Thomas M. Gorrie, Kendall Park, N.J.
[73] Assignee: Johnson & Johnson, New Brunswick, N.J.
[22] Filed: Jan. 2, 1974
[21] Appl. No.: 430,264

[52] U.S. Cl. ............................ 128/157; 128/132 D
[51] Int. Cl. .......................................... A61f 13/00
[58] Field of Search ........... 128/156, 157, 165, 160, 128/132 D; 161/249, 265; 2/61, 158, 168, 239

[56] References Cited
UNITED STATES PATENTS

| | | | |
|---|---|---|---|
| 1,301,708 | 4/1919 | Knutson | 128/157 W X |
| 2,446,371 | 8/1948 | Jones | 168/18 X |
| 2,653,601 | 9/1953 | Morrison | 128/165 |
| 2,703,573 | 3/1955 | Hamm | 128/156 |
| 3,097,644 | 7/1963 | Parker | 128/157 |
| 3,439,064 | 4/1969 | Makowski et al. | 161/249 X |
| 3,540,441 | 11/1970 | Collins | 128/157 X |

*Primary Examiner*—Aldrich F. Medbery

[57] ABSTRACT

A surgical wrap for covering or isolating extremities during surgical procedure is provided. The wrap provides a barrier to bacterial migration and is substantially conformable to the extremities. It is constructed to exhibit simultaneously the properties of stretchability and fluid-imperviousness. A manner of arranging the wrap into a form suitable for compact packaging and for facile application during surgery is also provided.

8 Claims, 10 Drawing Figures

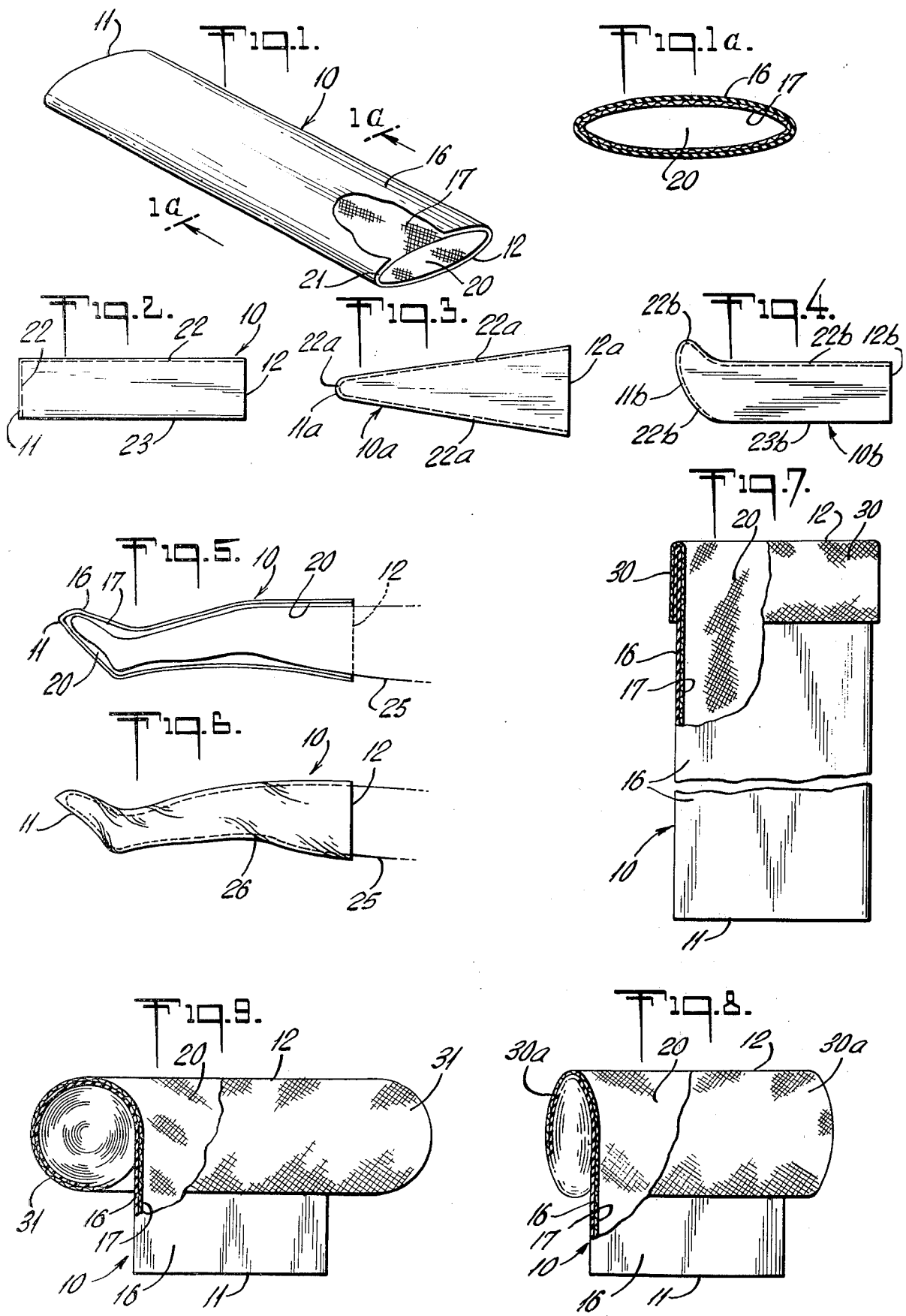

SURGICAL WRAP

The invention is directed to a surgical wrap and, more particularly to a novel covering for the extremities suitable for use during orthopedic surgery, and a manner of arranging the same for compactness and ease of application during surgery.

In surgical procedure, a patient is draped and/or otherwise covered with a sterile covering to prevent the prepared area of surgical interest from becoming contaminated by contact with unprepared areas or surfaces. In orthopedic surgery involving the extremities or parts proximate thereto such as hips and shoulders, special coverings are employed. In such surgery the extremity frequently must be manipulated during the course of the surgical procedure and a drape or a baggy or bulky covering is therefore unsuitable. It has been the practice to cover the extremity with a cotton stockinet. Although it is initially sterile and is applied in a sterile manner, once surgery has commenced, fluids, particularly blood and other body fluids, come into contact with it. When fluids have come into contact with and penetrate the non-impervious stockinet, the wet stockinet provides a path for bacterial migration and the sterile barrier is broken. The covering then becomes a source of contamination and the spread of infection, particularly when the limb is thereafter manipulated.

The terms "extremity" and "limb" are used interchangeably herein and will be meant to include the terminal portion of the limb as well as the limb, i.e. hand and arm or foot and leg.

It is an object of the present invention to provide a surgical extremity wrap or covering which is an effective barrier to bacterial migration throughout surgical procedure. It is further an object of the present invention to provide a covering which is substantially conformable to the shape of the extremity. A still further object of the present invention is to provide a wrap which may be facilely administered. These and other objects and such additional advantages as compactness for packaging as a disposable wrap may be realized according to the present invention.

The covering for the extremities suitable for use during surgery, particularly orthopedic surgery, is an elongated tubular wrap or envelope closed at one end and consisting of inner and outer layers. The inner and outer layers may be two separate envelopes concentrically positioned and operating conjointly or the two layers may be joined loosely such as only at the closed end, or firmly in a unitary construction to form inner and outer layers of a single envelope. The outer layer is fluid impervious. The inner layer has good slip-over properties (as hereinafter defined) and preferably is absorbent. Both inner and outer layers are stretchable, and preferably made of materials having some elastic properties. In a preferred embodiment of the present invention, an arrangement is provided which permits facile application to the limbs in preparation for surgery. Moreover, the extremity covering and arrangement thereof are particularly adaptable for use in prepackaged disposable coverings.

The present invention will be seen in the following description and accompanying drawings which illustrate a few embodiments contemplated by this invention and are not intended to limit the invention.

FIG. 1 is a perspective view of an extremity wrap of the present invention in the extended form from the open end.

FIG. 1a is a cross-sectional view taken along line 1a—1a of FIG. 1.

FIGS. 2–4 are side longitudinal views of some versions of extremity wraps in accordance with the present invention.

FIG. 5 is a longitudinal sectional view of an extremity wrap applied to the leg and foot of a patient.

FIG. 6 is an elevational view of a wrap which has been twisted about a leg and foot to increase conformability.

FIG. 7 is an elevational view partially in section of an extremity wrap at the initial folding stage of a cuff fold.

FIG. 8 is an elevational view partially in section of a folded extremity wrap folded in a cuff fold.

FIG. 9 is an elevational view partially in section of an extremity wrap rolled in a toroidal roll.

Referring now more particularly to the drawings, and especially to FIG. 1, the numeral 10 denotes the extremity covering or wrap which is tubular in form and closed at one end 11 and open at the other end 12 in the manner of an elongated envelope for the insertion of an extremity. The wrap consists of an outer tubular layer 16 and an inner tubular layer 17 concentrically positioned so that when the limb is covered by the wrap, the limb is positioned in the tubular chamber 20 immediately surrounded by the inner tubular layer, which in turn is surrounded by the outer tubular layer. This is also seen in cross-section in FIG. 1a. The wrap is designed to receive either extremity, a foot and leg, or a hand and arm.

The inner and outer layers are formed of stretchable material. The outer layer further is made of a fluid-impervious material. Suitable materials for the outer layer are preferably elastomeric materials such as styrene-butadiene rubber, natural rubber and butyl rubber. Other typical stretchable materials which may be employed include ethyl vinyl acetate, polyvinyl chloride, polyethylene, etc. These materials are non-supportive of microbial growth and further prevent transmission of body fluids to the inner layer and to the body. The outer layer may be fabricated from thin, flexible sheeting or film made from blown tubing, cast tubing, etc. to which closure means as necessary are provided to form the tubular envelope or wrap as above described. Such necessary end and peripheral closures may be achieved by folds or any suitable closure means known to the art, such as a heat seal. In addition, the end closure may be achieved by tying or even clamping just prior to use, but the preferred embodiment employs a previously formed seal or a fold.

The inner layer is made of stretchable materials with good slipover properties. The expression "good slip-over properties" is meant a non-clinging or non-sticking property which permits ease of application. It is not intended that the inner layer be slippery. Both stretchability and good slip-over properties may be achieved with textile materials. Stretchability may be achieved by the manner of construction of the fabric, e.g. knitting. Knitted fabrics are preferred. However, textile materials in other forms such as woven fabrics, especially when cut on a bias, or even nonwoven fabrics with stretchable inserts may be employed. It is preferred, although not essential that the inner layer be at least somewhat absorbent. This is desirable primarily from the standpoint of comfort to the patient. Organic textile materials of natural or synthetic fibers such as cotton, linen, rayon, polyesters, polypropylene, etc. may be employed. Cotton and rayon are among the preferred materials. The end and other peripheral closures as necessary in the inner layer are conveniently achieved by stitching, although tying and other methods may be employed.

Further requirement for materials for both outer and inner layers is that the materials be stable to sterilization techniques. Additionally, the outer covering material must meet the anti-static properties required for operating rooms.

Since the covering is for the limbs in a passive state and since the materials of construction are to be of a stretchable nature, it is not critical and essential that the tubular wrap have the exact outline of the extremity it is covering to satisfy the objective of a substantially conformable wrap. However, the covering must not hang loosely or slide around and is thus distinguished from a drape or a loose-fitting covering. Thus, the tubular wrap may have any of a number of forms some of which are shown in FIGS. 2–4, as well as other forms not shown, such as, for example, a wrap having the terminal portion in a mitt-like configuration for enclosing a hand.

FIGS. 2–4 are side views of some of the various shapes of tubular wrap 10. FIG. 2 illustrates a wrap which is not preshaped. It has a generally cylindrical configuration in which the closed end 11 is of the same width as the open end 12. A generally conical shape is seen in the wrap 10a of FIG. 3 where the closed end 11a is of substantially smaller width than the open end 12a. A shape outlining the foot at the closed end 11b is seen in wrap 10b of FIG. 4, having open end 12b.

The peripheral closures may be accomplished by seals or folds or a combination of seals and folds. FIGS. 2–4 illustrate some ways in which this may be accomplished. Thus, in FIGS. 2–4 the peripheral closures are accomplished by seals 22, 22a or 22b and folds 23 or 23b. Other modifications may be employed. Thus, in a wrap having a shape generally as shown in FIG. 2, the peripheral closure along both longitudinal edges may be a fold with a seal closure at the end. Alternatively, the end closure may be a fold with a seal along both longitudinal edges.

FIG. 5 is a cross-sectional view of the extremity wrap of the type shown in FIG. 2 applied to a human foot and leg. In FIG. 5, an extremity (foot and leg) 25 is positioned in a tubular chamber 20, surrounded by and in substantial but incomplete contact with inner layer 17 which in turn is surrounded by outer layer 16. It shows the substantial conformance to the foot and leg which may be achieved even if the envelope is not pre-shaped in the outline of a foot and leg. Such conformance is deemed ample for surgical procedures in the upper portion of the extremity or in areas adjacent to the extremity. Thus, FIG. 2 illustrates a preferred configuration of the wrap of the present invention. When greater conformance is desired, such as in surgery in the narrower lower part of the leg, it may be achieved by a slight twisting of the wrap. FIG. 6 illustrates how a non-pre-shaped wrap such as illustrated in FIG. 2 may be slightly twisted to increase conformability. Wrap 10 is shown with puckers 26 resulting from twisting as it is extended over limb 25 (dashed lines).

Similar considerations are applicable when the extremity being considered is the arm and hand.

Although the invention has been discussed in terms of the inner and outer layers being separate entities, the inner and outer layers may be joined at the closed end, along its length or throughout to form the inner and outer layers of a single extremity wrap. When such is desired the inner and outer layers may be joined by any suitable adhesive known to the art such as, for example, an acrylate. However, in operation the two member wrap has been found to be completely satisfactory and no significant benefit is expected to be gained by joining the two members.

The extremity wrap may be made in different sizes. Thus when the wrap is contemplated as a leg covering, a larger size would be chosen than when used as an arm covering. Generally, the dimensions may vary from about 4 to 14 inches in flat width and correspondingly from about 20 to 50 inches in length. (By flat width is meant the width across the flattened tubular wrap.) Preferred dimensions for use as extremity covering for adults are about 8 to 10 inches in flat width and 45 to 50 inches in length. The inner layer preferably has slightly smaller dimensions. The flat width may be as much as 2 inches smaller. The length of the inner layer may be the same or slightly less. If the length is slightly less, the outer layer will completely cover the inner layer when the wrap is fully extended. It is not critical and essential that the outer layer be longer than the inner layer for the outer layer may be tucked inwardly toward the limb over the inner layer and in this way protect the inner layer from contact and contamination.

Since it is now becoming the practice of hospitals to use prepackaged coverings which are generally disposable, it is desirable that the extremity wrap be available in a compact form and easy to handle in operating room procedure.

A further aspect of the present invention is an improved means for packaging, handling and applying the fluid-impervious extremity wrap of the present invention.

To achieve a compact form the extremity wrap may be folded or rolled. The folding or rolling may be accomplished in numerous ways. Thus, the wrap may be arranged in an accordian fold or in a tubular roll in which the width of the wrap forms the core around which the wrap is rolled. While these arrangements provide compact units useful for packaging, they are less advantageous for handling in the surgical arena, for wraps so folded or rolled do not permit the closed end to be immediately placed at the terminal portion of the extremity. The arranged extremity wrap of the present invention permits facile application by immediate placeability of the wrap at the terminal portion of the extremity followed by covering of the entire or such portion of the limb as desired as the wrap is extended. One improved arranged extremity wrap of the present invention is a folded wrap, folded in a cuff-fold. A further improved arranged extremity wrap of the present invention is a rolled wrap, rolled in a toroidal or doughnut-like roll.

FIGS. 7 and 8 show initial and final stages of folding in a cuff-fold to a compact form suitable for commercial packaging. FIGS. 7 shows wrap 10 with open end 12 and closed end 11 and cuff 30. FIG. 8 shows a shortened wrap 10 with open end 12 and closed end 11 and cuff 30a.

In preparing the folded extremity wrap, the inner and outer layers are simultaneously folded outwardly in a cuff-fold to form a cuff 30 wherein the inner layer is the visible portion of the cuff. The initial fold is of from about one-fourth to about one-half of the flattened width of the wrap. This folding is repeated until the closed end of the wrap is approached and a compact size is achieved. FIG. 8 shows the extremity wrap in the finally folded form. The cuff in the finally folded form is seen at 30a.

FIG. 9 shows the extremity wrap 10 with the open end 12 and closed end 11 in the final stage of rolling in a toroidal roll 31 to a compact form suitable for commercial packaging.

In preparing the rolled extremity wrap, the inner layer is rolled outward onto the outer layer in a cuff-like manner so the inner layer forms the visible covering of the roll. The rolling is continued until a compact form as shown in FIG. 9 is obtained.

To use the extremity wrap of the present invention in the surgical arena, the arranged wrap is removed from its protective covering and is handled using aseptic techniques with the hands grasping the folded or rolled cuff. The covering in the arranged form is placed on the terminal portion of the extremity at the closed end and pulled away from the terminal position unfolding or unrolling as the operator proceeds up the prepared extremity or limb to the distance desired. If the extremity wrap is not completely extended, the portion remaining is folded or tucked inwardly so that the inner layer is protected by the impervious outer layer. The limb is then ready for further surgical procedures. If surgery is to be accomplished on the limb itself, the conformable nature of the wrap permits the making of an incision through the wrap and optional placement of an incise drape, surgical towels, etc. and/or conduction of other procedures. Conformability may be increased, if desired, by twisting as previously described prior to the making of an incision. The outer layer is non-supportive of microbial growth and its fluid-impervious nature inhibits fluids and microorganisms from reaching the inner layer and body area.

It is to be understood that the foregoing is merely exemplary and the present invention is not to be limited to the specific form or arrangement of parts herein described and shown.

What is claimed is:

1. Surgical draping means for providing ease of aseptic application and close fit of a surgical drape to a body extremity, said draping means comprising a sterile, elongated tubular wrap, closed at one end and open at the other end, and having substantially coextensive inner and outer layers, said inner layer comprising a stretchable, textile material with good slip-over properties, and said outer layer comprising a thin, fluid impervious, elastic drapable material which is a barrier to bacterial migration and meets the antistatic properties required for operating rooms.

2. The drape of claim 1 which is in a compact, cuff-folded configuration, said inner layer overlying said outer layer, said configuration comprising a series of cuff folds of from about one-fourth to about one-half of the flat width of the wrap, the total width of the folded wrap being substantially that of a single said cuff fold.

3. The drape of claim 1 which is in the form of a torroidal roll, said inner and outer layers having been simultaneously rolled circumferentially outward from said open end in a two-layer torroidal roll until said roll has approached said closed end.

4. Draping means according to claim 1 wherein the inner and outer layers are separate units concentrically positioned.

5. Draping means according to claim 1 wherein the inner and outer layers are joined.

6. Draping means according to claim 1 wherein the inner layer is made of an organic textile fiber and the outer layer is made of an elastomer.

7. Draping means according to claim 6 wherein the inner layer is made of cotton and the outer layer is made of styrene-butadiene rubber.

8. Draping means according to claim 1 wherein the inner layer is made of a knitted fabric and the outer layer is made of a thin elastomeric sheeting.

* * * * *